United States Patent [19]
Sayag et al.

[11] Patent Number: 5,510,623
[45] Date of Patent: Apr. 23, 1996

[54] CENTER READOUT INTRA-ORAL IMAGE SENSOR

[75] Inventors: Michel Sayag, Mountain View; Steven Onishi, San Jose, both of Calif.

[73] Assignee: Loral Fairchild Corp., Syosset, N.Y.

[21] Appl. No.: 394,149

[22] Filed: Feb. 24, 1995

[51] Int. Cl.$^6$ .............................. H04M 5/32; G01T 1/20
[52] U.S. Cl. .................................. 250/370.11; 250/208.1; 250/370.09; 257/222; 257/225; 348/311; 378/988; 378/191
[58] Field of Search .................... 250/208.1, 370.09, 250/370.11; 378/98.8, 191, 40; 348/311, 324; 257/222, 225, 231, 232

[56] References Cited

U.S. PATENT DOCUMENTS

| | | | |
|---|---|---|---|
| 4,179,100 | 12/1979 | Sashin et al. | 250/366 |
| 4,426,721 | 1/1984 | Wang | 378/99 |
| 4,647,977 | 3/1987 | Tower | 348/321 |
| 4,783,225 | 11/1988 | Maejima et al. | 148/33.2 |
| 4,946,238 | 8/1990 | Sashin et al. | 350/96.27 |
| 4,996,413 | 2/1991 | McDaniel et al. | 250/208.1 |
| 5,008,547 | 4/1991 | Molteni et al. | 250/368 |
| 5,037,207 | 8/1991 | Tomei et al. | 356/444 |
| 5,109,159 | 4/1992 | Hagiwara et al. | 250/368 |
| 5,113,077 | 5/1992 | Shimizu et al. | 250/370.11 |
| 5,140,162 | 8/1992 | Stettner | 250/370.11 |
| 5,142,557 | 8/1992 | Toker et al. | 378/37 |
| 5,151,588 | 9/1992 | Kiri et al. | 250/208.1 |
| 5,187,380 | 2/1993 | Michon et al. | 257/428 |
| 5,230,747 | 7/1993 | Maejima et al. | 148/33.2 |
| 5,279,992 | 1/1994 | Maejima et al. | 437/229 |
| 5,291,010 | 3/1994 | Tsuji | 250/208.1 |
| 5,331,166 | 7/1994 | Yamamoto et al. | 250/370.11 |
| 5,331,961 | 7/1994 | Inaba et al. | 128/659 |
| 5,340,988 | 8/1994 | Kingsley et al. | 250/370.09 |
| 5,369,281 | 11/1994 | Spinnler et al. | 250/370.09 |
| 5,434,418 | 7/1995 | Schick | 250/370.11 |

FOREIGN PATENT DOCUMENTS

| | | |
|---|---|---|
| 429977A | 6/1991 | European Pat. Off. |
| 574690A2 | 12/1993 | European Pat. Off. |
| 2533515A | 1/1986 | Germany . |
| 1-254888 | 10/1989 | Japan . |
| 3-165291 | 7/1991 | Japan . |
| 3-189585 | 8/1991 | Japan . |
| 5-130991 | 5/1993 | Japan . |

*Primary Examiner*—Carolyn E. Fields
*Attorney, Agent, or Firm*—Perman & Green

[57] ABSTRACT

A solid state image sensor CCD array (10a) has a two block, full-frame, parallel-register structure. The two blocks of the array, each comprised of photosensitive radiation sensors or pixels (20), feed into a single centrally disposed serial read-out register (10b) so as to form one unified photosensitive domain. The read-out register is photosensitive except for two associated narrow clock buses (H1, H2) that are spaced apart so as to only block a minimum of input radiation in any one pixel (22) of the read-out register. Each stage of the read-out register can act as a pixel that is approximately square and that is approximately the same size as the pixels of the two full-frame blocks. In operation, the centrally disposed read-out register can be stationary for a significant first portion of a total frame time (integration period), and then in a latter part of the frame time it can be read out one or more times to provide exposure update information for all of the pixels of the array. Typical examples of applications include advanced histogram-based, or other types of, X-ray exposure optimization. The array avoids the use of an "amplifier corner" that is characteristic of most if not all area image sensors. As such, all four corners of the array can be shaped to suit a particular application. One application of particular interest is for intra-oral dental X-ray imager and system.

20 Claims, 11 Drawing Sheets

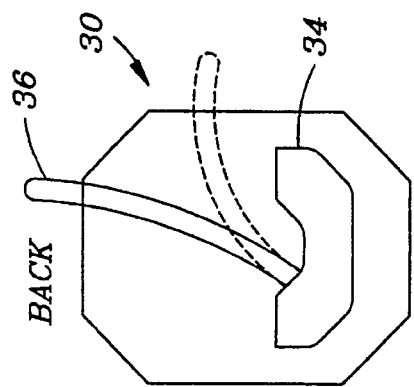
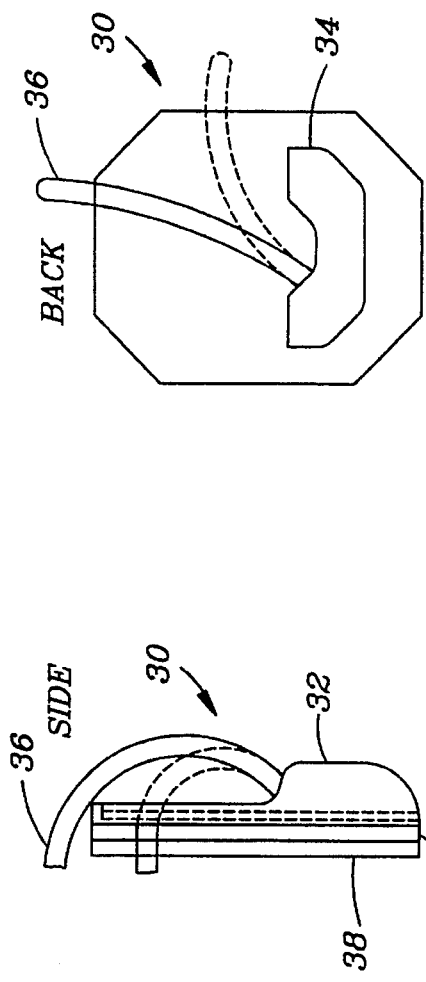
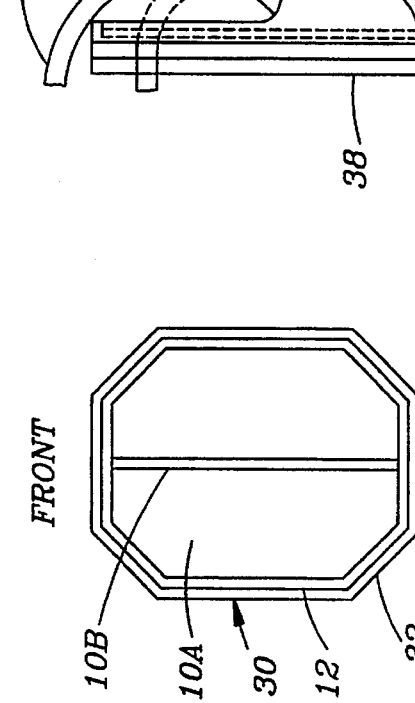
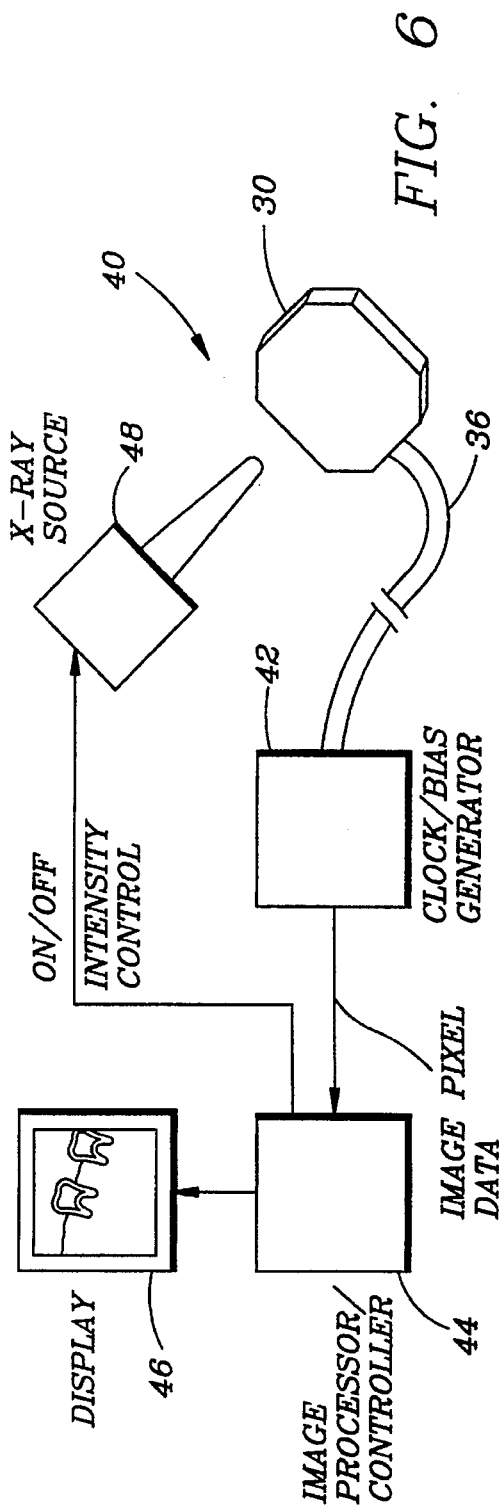

CENTER READOUT INTRA-ORAL IMAGE SENSOR

FIELD OF THE INVENTION

This invention relates generally to imaging devices and, in particular, relates to X-ray images sensors, for example dental X-ray image sensors, that employ a charge-coupled-device (CCD) readout device.

BACKGROUND OF THE INVENTION

The use of photodetectors as sensors of fluorescent radiation emitted by an X-ray responsive material are known in the art. By example, U.S. Pat. No. 4,996,413, entitled "Apparatus and Method For Reading Data From an Image Detector" by McDaniel et al., describes an n×m array of photodetectors (a non-CCD, MOS-type imager). Image information is read-out by sequentially selecting groups of rows starting with a row near the middle of the array and then sequentially selecting other groups of rows on alternative sides of the array middle. The array is said to be divided into two groups of detector elements in order to decrease an amount of time to read-out the signal from each detector element in the array (col. 4, lines 49–52, col. 5, line 57 to col. 8, line 8). In this system an image processor 28 is said to produce a brightness control signal which is fed to an exposure control circuit 34 to regulate an X-ray tube power supply 16 and thereby the X-ray exposure (col. 3, lines 24–27).

Such MOS-types of photodetector arrays include rather large peripherally-located scan generators and structures which place constraints on the shape that the array can take.

The use of a charge coupled device (CCD) to record light emitted from a phosphor screen in response to X-rays is also known in the art. By example, in U.S. Pat. No. 5,142,557, entitled "CCD And Phosphor Screen Digital Radiology Apparatus And Method For High Resolution Mammography", Toker et al. describe the use of a CCD camera 20 having a cooled CCD array and a MIN-R phosphor screen 4. FIG. 5 shows an embodiment where a fiber optic reducer 45 is placed between the phosphor screen 4 and the CCD camera 20. FIG. 6 shows a parallel CCD array 61 and a CCD serial register 62. During an exposure clocks to the parallel array 61 are stopped, while serial register 62 is clocked and read-out to monitor the accumulated light exposure. A computer 65 generates a signal to terminate the X-ray dose as soon as a certain minimum acceptable threshold dosage is received (col. 9, line 16 to col. 10, line 37). An externally generated signal is required to indicate that the exposure has begun (col. 9, line 67 to col. 10, line 1).

In the approach of Toker et al. the location of the serial CCD register 62 is not specified and, from its connectivity with the parallel array 61 in FIG. 6, would appear to be external to the parallel array as is the case with most if not all CCD image sensors.

For example, it is known that dental X-ray sensors have been constructed with a simple rectangular CCD array having a linear readout register along one edge, although it is not known if any of the edges of such arrays have been beveled, or if the readout register has been employed also for other purposes.

In U.S. Pat. No. 5,331,166, entitled "Dental X-ray Image Detecting Device With an Automatic Exposure Function" by Yamamoto et al., there is described a medical X-ray image detecting device that includes an X-ray intensity detecting element that is located in a casing adjacent to an X-ray image sensor. The image sensor further includes a CCD device located on a ceramic substrate, and glass fiber bundles disposed between the CCD and an X-ray fluorescent element.

In U.S. Pat. No. 5,291,010, entitled "Solid State Imaging Device Having a Chambered (sic, Chamfered) Imaging Device Corner" by Tsuji, there is described a CCD having two corners that are chamfered and that is located within an electronic endoscope.

Other U.S. patents of interest in this area include U.S. Pat. Nos. 4,426,721; 5,113,077; 5,140,162; 5,142,557; 5,187,380; 5,340,988; 4,179,100 and 5,369,281. Also of interest are Japanese Patents 403165291 A; 403189585 A and 405130991 A; European Patents 000574690 A2 and 00429977 A; and German Patent 3522515.

OBJECTS OF THE INVENTION

It is an object of this invention to provide an improved CCD imaging sensor and an improved CCD imaging sensor for use in an X-ray imaging application, such as a dental X-ray imaging application.

It is a further object of this invention to avoid the use of any CCD read-out registers at peripheral regions of the CCD array so as to enable the array to be shaped, without constraint, to conform to a desired physical configuration.

It is another object of this invention to provide a CCD imaging sensor that has a single centrally disposed photo-responsive read-out register for providing a read-out of charge packets from first and second halves of an array, while also enabling radiation exposure monitoring and radiation exposure initiation and termination monitoring.

It is one still further object of this invention to provide a CCD imaging sensor having a "zippered" architecture for feeding charge packets into a centrally disposed read-out register.

SUMMARY OF THE INVENTION

The objects of the invention are realized by a solid state image sensor array having a two block, full-frame, parallel-register structure and a single, shared central read-out register. In a presently preferred embodiment the image sensor array is a CCD-device that is employed as a part of an X-ray image sensor.

The two blocks of the array, each comprised of photosensitive radiation sensors or pixels, feed into a single, centrally-disposed serial photosensitive read-out register so as to form one unified photosensitive domain. The read-out register is photosensitive except for two associated narrow clock buses that are spaced apart so as to only block a minimum of input radiation in any one pixel of the read-out register. Each stage of the read-out register can act as a pixel that is approximately square and that is approximately the same size as the pixels of the two full-frame blocks.

In operation, the centrally disposed read-out register can be stationary for a significant first portion of a total frame time (integration period), and then in a latter part of the frame time it can be read out one or more times to provide exposure update information for all of the pixels of the array.

This exposure information is especially valuable in those applications wherein pixels near the center of the array are desired to be monitored. Typical examples of such applications include advanced histogram-based or other types of exposure optimization.

In a further embodiment the centrally disposed read-out register can be stationary for the entire frame time, and then read out to form a part of the final image.

In that the image sensor array of this invention avoids the use of an "amplifier corner" that is characteristic of most if not all area image sensors, all four corners of the array can be shaped to suit a particular application. One such application of particular interest herein is for intra-oral dental X-ray imaging, where it is beneficial to have all four corners cut back or chamfered so as to minimize patient discomfort, and for other applications where space is limited and where it is advantageous to have all four corners of the array truncated or rounded.

BRIEF DESCRIPTION OF THE DRAWINGS

The above set forth and other features of the invention are made more apparent in the ensuing Detailed Description of the Invention when read in conjunction with the attached Drawings, wherein:

FIG. 4A is a front view, FIG. 4B is a side view, and FIG. 4C is a back view of an intra-oral sensor package in accordance with this invention;

FIG. 6 is a block diagram of an x-ray system in accordance with this invention;

DETAILED DESCRIPTION OF THE INVENTION

Figure 1:
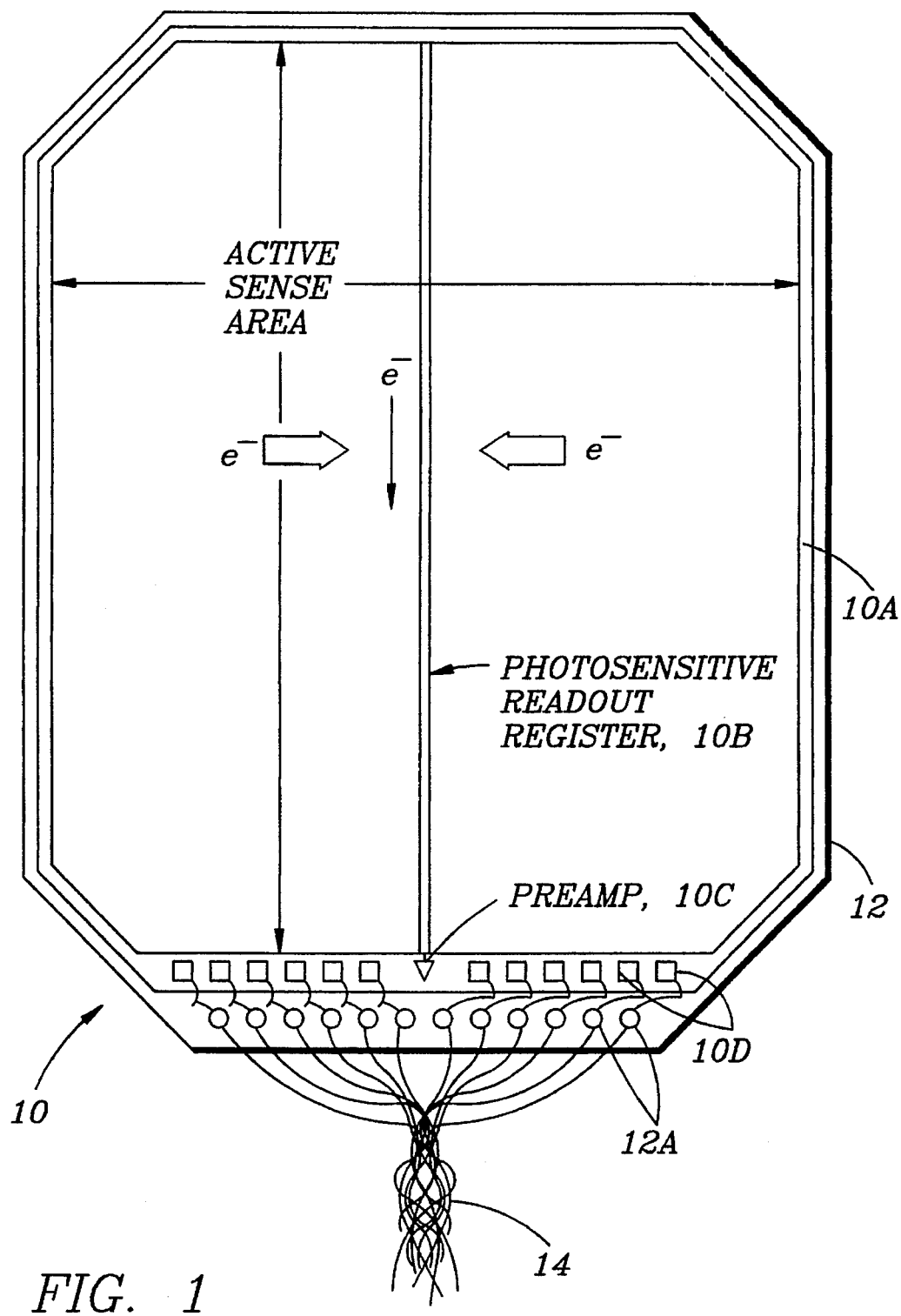
FIG. 1 is an enlarged plan view, not to scale, of a CCD radiation sensor array in accordance with this invention.

FIG. 1 illustrates a plan view an X-ray silicon image sensor chip 10 in accordance with this invention. Although described below in the context of an intra-oral X-ray image sensor, it should be realized that the use of the image sensor 10 is not limited to only this one application.

The silicon image sensor chip 10 is a silicon-based CCD having an area array 10a comprised of individual pixels that are approximately 40 microns×40 microns square. The CCD gate structure is generally fabricated using three successive polysilicon (poly) depositions. The overall active sensing area is a rectangular region approximately 25 mm×30 mm. All four corners of the array 10a are preferably chamfered (or bevelled). The approximate array size is 640 pixels by 800 pixels. FIG. 1 also illustrates a substrate or carrier 12 on which the Si CCD area array 10a is mounted. The corners of the carrier 12 are also bevelled to match the corners of the array 10a. The diagonal dimensions of the array 10a and the carrier 12 are thus both beneficially reduced by approximately 10% due to the bevelling of the array 10a and the carrier 12.

The array 10a includes a centrally disposed photosensitive read-out register 10b (also referred to herein as a horizontal (H) register) that is coupled to an output charge-sensing preamplifier (preamp) 10c. The preamp 10c converts a magnitude of a charge packet to a corresponding voltage potential.

In accordance with an aspect of this invention the read-out register 10b is placed so as to divide or partition the active area of the array 10a into two halves (referred to herein for convenience as left and right halves or as top and bottom halves). A plurality of terminals 10d are disposed along one edge of the array 10a, and are wirebonded to corresponding terminals 12a on the carrier 12. Wiring 14 is connected to the terminals 12a for connecting the array 10a to suitable DC operating power, biases, clock signals, and for outputting the charge signals from preamp 10c. The charge signals are read-out of the array 10a either after an exposure or during the exposure.

In accordance with an aspect of this invention the CCD read-out structure is disposed at an interior region of the array, in this case in the center (read-out register 10b), as opposed to along edges that extend to rectangular corners of the array. Only the preamp 10c is located at an edge of the array, with the preamp being disposed at one end of the readout register 10b, away from the corners, as opposed to being located in a corner. This enables the outer edges of the array 10a to be shaped as desired. For example, a regular octagon shape can be used wherein each edge is equal in length to all other edges.

Figure 2:
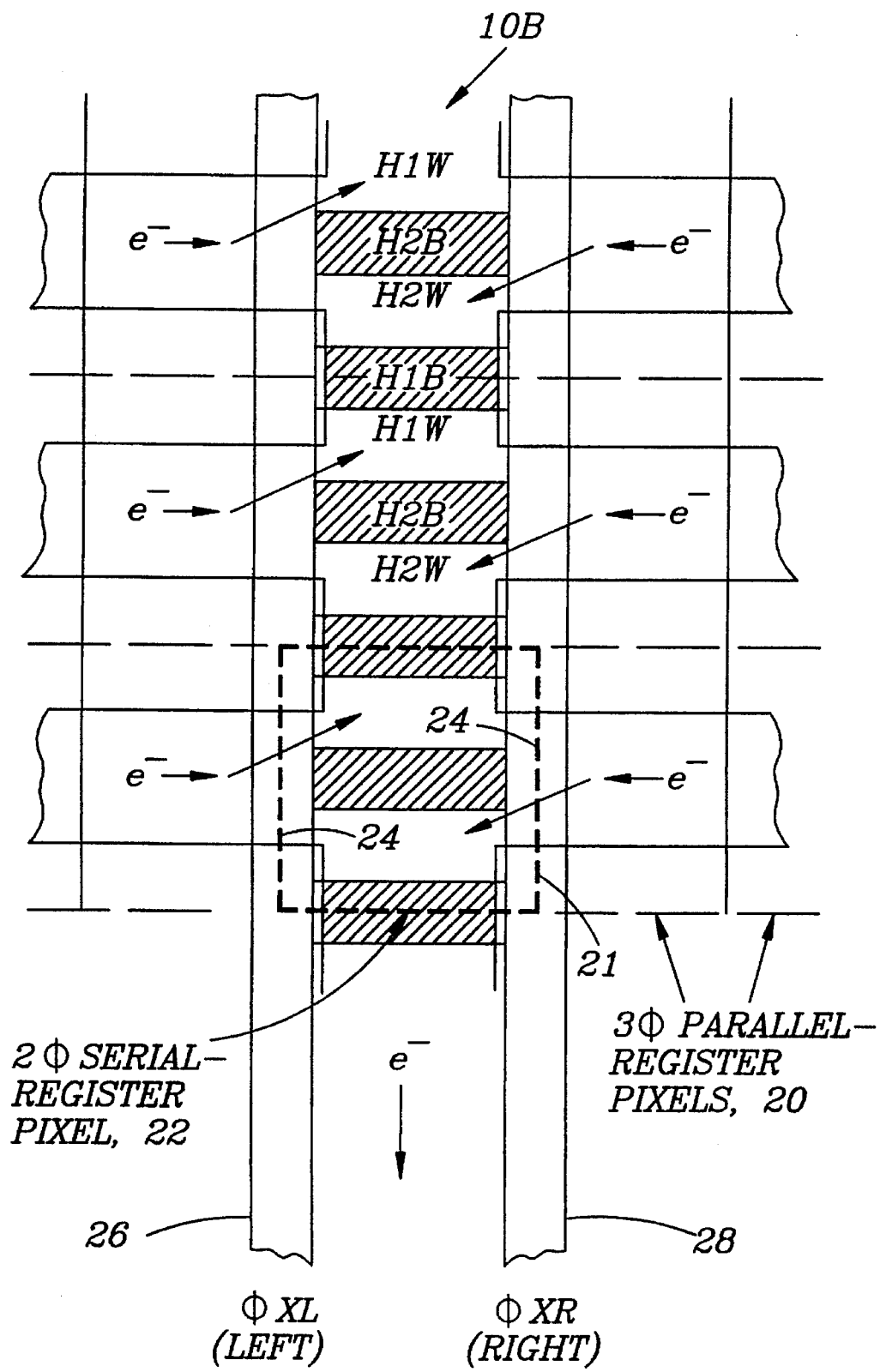
FIG. 2 is an enlarged, simplified view, not to scale, of a portion of the array of FIG. 1, the Figure specifically showing the interface between a center read-out register (horizontal register) and adjacent parallel registers (vertical registers)
Figure 3:
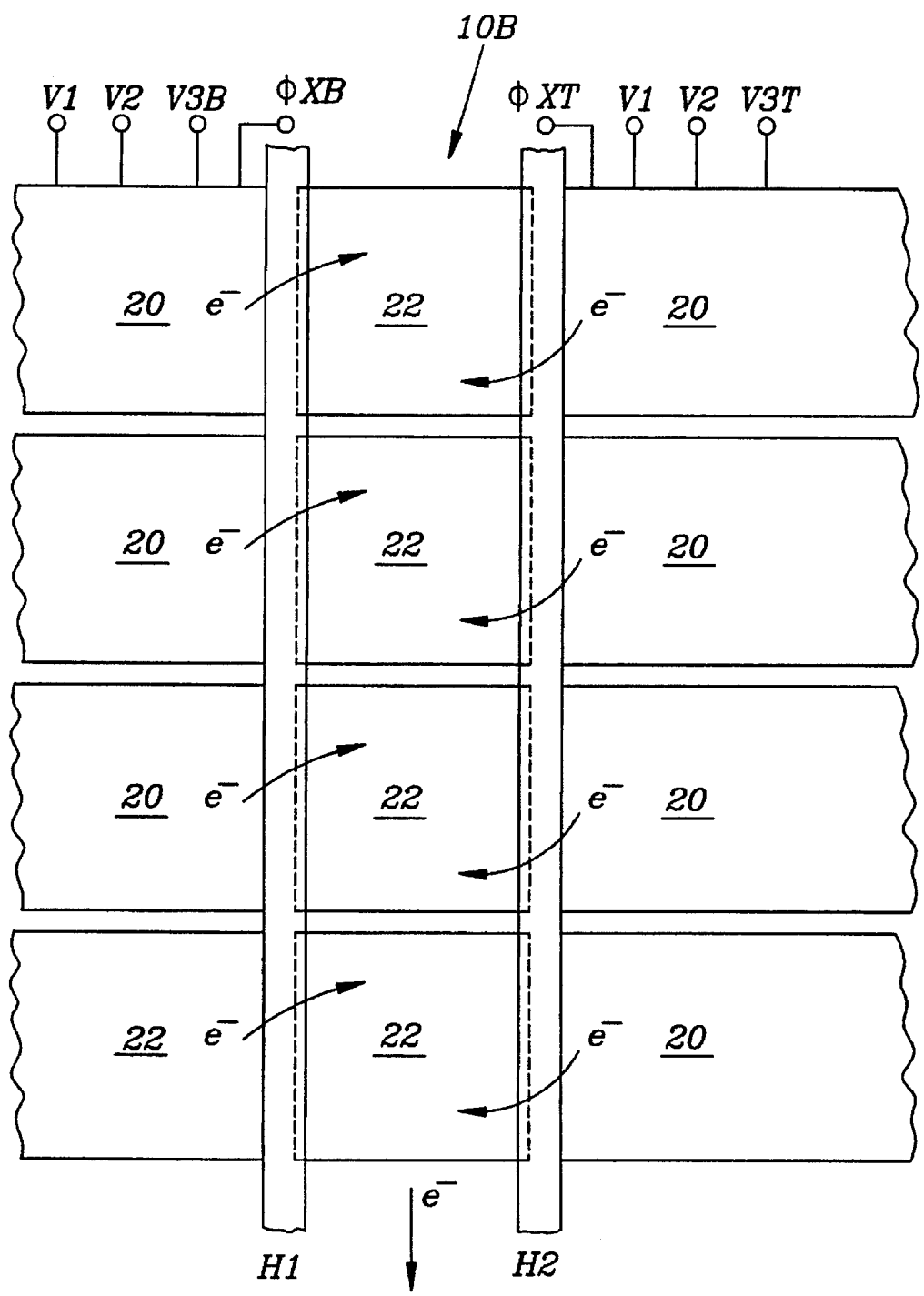
FIG. 3 is another enlarged, simplified view, not to scale, of a portion of the array of FIG. 1, the Figure showing in greater detail the two phase center read-out register buses and their parallel orientation with the center read-out register pixels.

FIGS. 2 and 3 illustrate a portion of the read-out register 10b and associated structure. In particular, there are illustrated a plurality of three phase parallel-register pixels 20 (also referred to herein as vertical (V) registers) and a plurality of two phase serial-register pixels 22. In this embodiment all of the pixels have dimensions of approximately 40 microns×40 microns. The boundaries of the parallel-register pixels 20 are defined by the centers of channel stop regions in one direction and by the centers of one of the phases in the other direction (generally this is the multi-phase pinned (MPP) barrier phase). The boundary between the parallel-register pixels 20 and the serial-register pixels 22 is located at the center of a transfer gate 24. There is a transfer gate 24 on both the left and right sides of each pixel 22 of the serial read-out register 10b. The boundaries between the serial-register pixels 22 are the centers of one of the two phase barriers of each stage of the read-out register 10b. The structures designated as H1W and H2W are horizontal wells, while the structures designated as H1B and H2B are horizontal barriers.

The MPP type of CCD register or CCD array is one that provides especially low dark signal, and is generally beneficial in improving the sensitivity of the sensor.

FIG. 3 shows the two phase H1 and H2 metal buses that run parallel to and that slightly overlap the pixels 22 of the read-out register 10b. It is noted that any transfer gate metalization 26 and 28 can be placed outside the array. The CCD chip 10 is fabricated with three layers of polysilicon, and space is provided in the region of these H1 and H2 buses and the transfer gates 24 for contacts and other layout considerations.

The parallel registers from the two halves of the sensor array 10a are preferably fabricated with small-angle bends so as to create a "zipper" configuration. This zipper layout provides an advantage in achieving a high-performance, high-yielding design. The zipper configuration layout minimizes the effective transfer gate length which improves the charge transfer efficiency, while maintaining reasonable Poly dimensions in the overall layout.

It should be realized that even if the pixel boundaries are on a precisely uniform square grid, the responsivities of the three types of pixels (interior parallel region pixels 20, interface pixels 21, and read-out pixels 22) will not necessarily be matched. Any difference in responsivity is, however, not detrimental to the operation of the array 10 since there will generally be a uniformity correction capability in the image processing system 44 (FIG. 6) to which the array 10a is coupled during use. The responsivity of the interface pixels will tend to be less due to the presence of one metal serial clock bus (H1 and H2) per side. Also the different types of pixels will tend to differ in responsivity due to different (semitransparent) polysilicon layouts.

There are a number of methods to scan charge packets (indicated as e⁻) out of the array 10a. In order to explain the preferred embodiment, a first, least complex embodiment is described. In the first embodiment there are independent 3-phase clocks on the left and the right sides of the array 10a. In scanning the array 10a, a first side (left or right) of the array is held stationary while the second side in scanned; then the first side is scanned. The minimum number of clocks for this type of operation is six, which includes the clocks for the transfer gates 24. That is, in this embodiment it is not necessary to have separate clocking of the transfer gates 24, in that they can be driven by the Phase-3 (MPP barrier phase) clock.

In another read-out method embodiment, described in greater detail below, the two halves of the sensor 10 are instead read out in an alternating-line sequence, with some clocks (V1 and V2) being shared between the two halves. In this mode the charge packets move toward the read-out register 10b in lock-step until they reach a phase just preceding the transfer gate 24. This phase is referred to herein as a holding phase. For this read-out method there are only three parallel register transport clocks, two transfer gate clocks, and one additional clock for one of the holding phases. Although the total number of clocks is the same as in the first embodiment, this second embodiment has certain advantages for some layout configurations.

FIG. 2 shows a first, relatively simple transfer gate embodiment. Alternatively the transfer gate could be of the composite implanted barrier type, having both a barrier gate electrode and a non-barrier gate electrode.

Figure 5A:
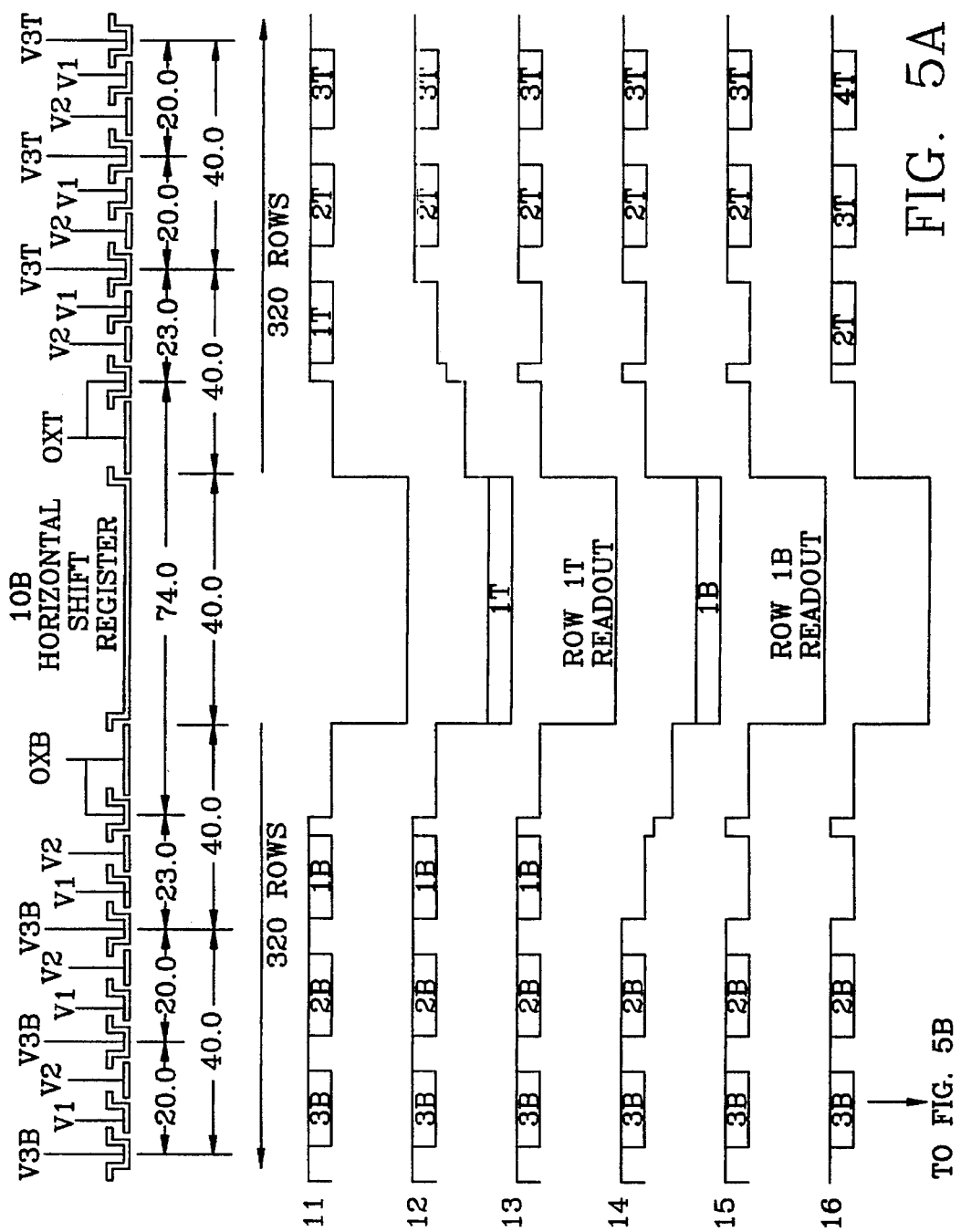
FIG. 5 illustrates a timed sequence of charge packet movement towards the central read-out register under control of three phase vertical register clocks.
Figure 5B:
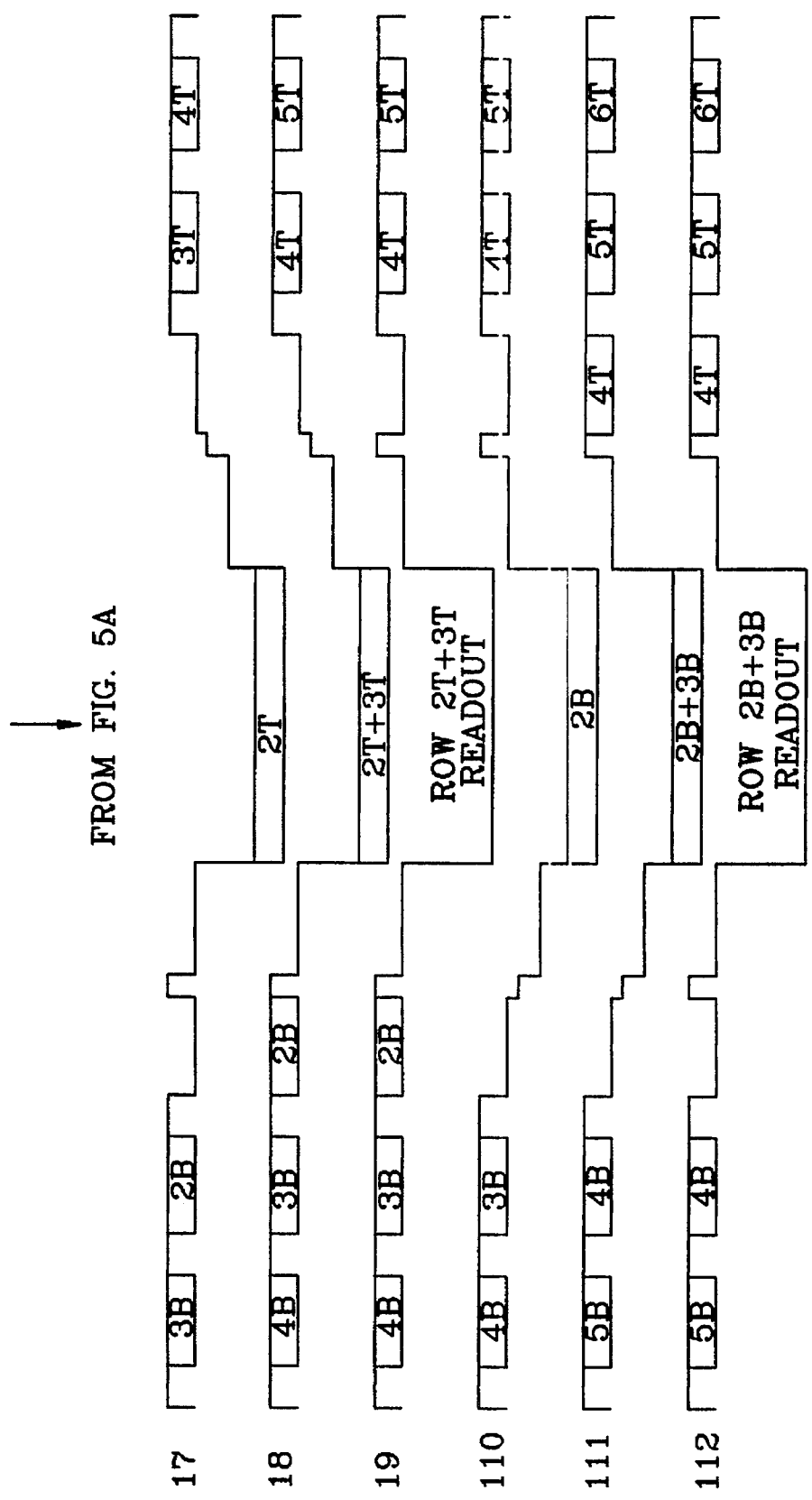
Figure 7:
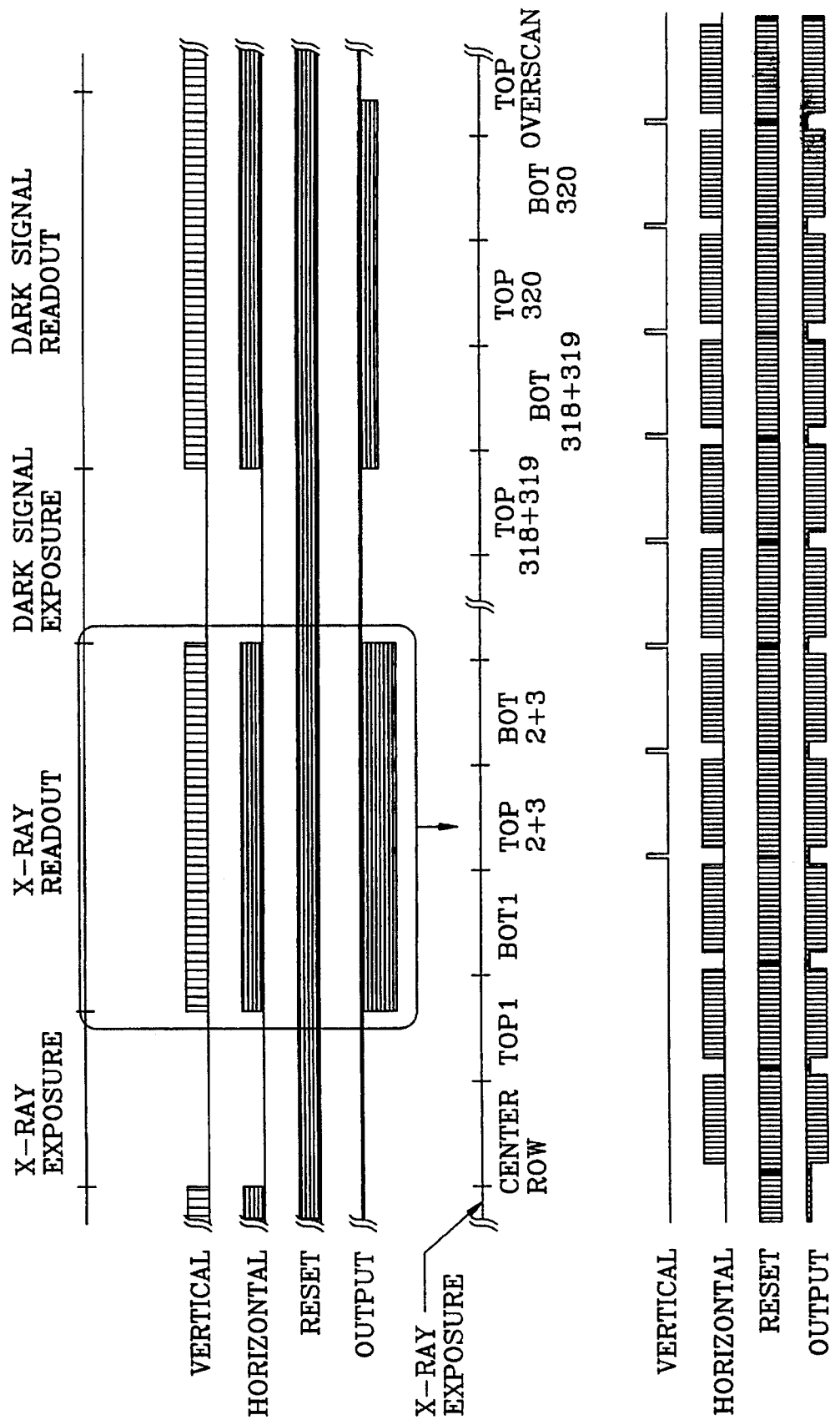
FIG. 7 is an overall timing diagram illustrating the clocking of the array before, during, and after an X-ray exposure.
Figure 8:
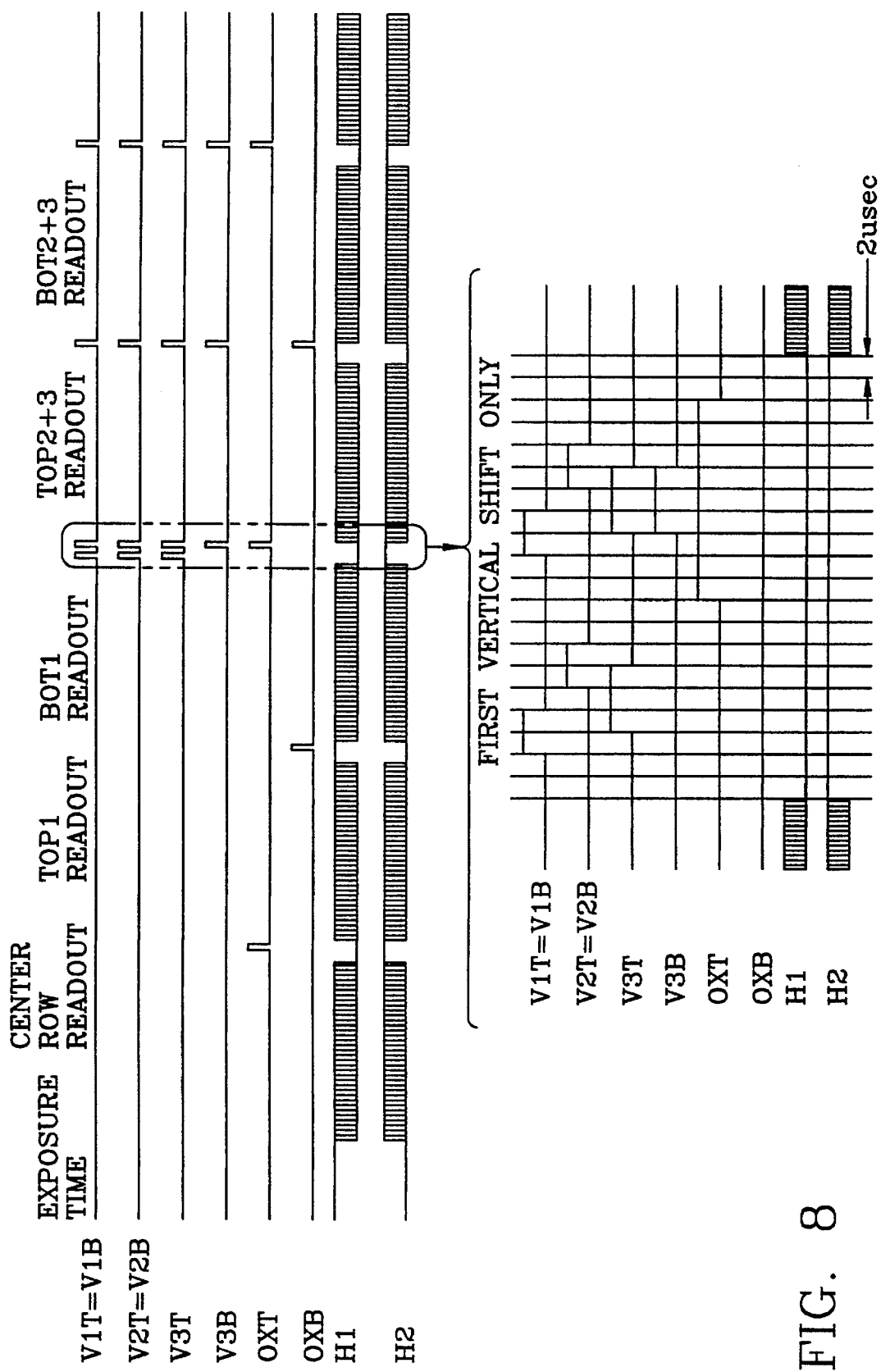
FIG. 8 illustrates vertical register clocks and horizontal register clocks, and shows in detail the timing for the first vertical register shift.
Figure 9A:
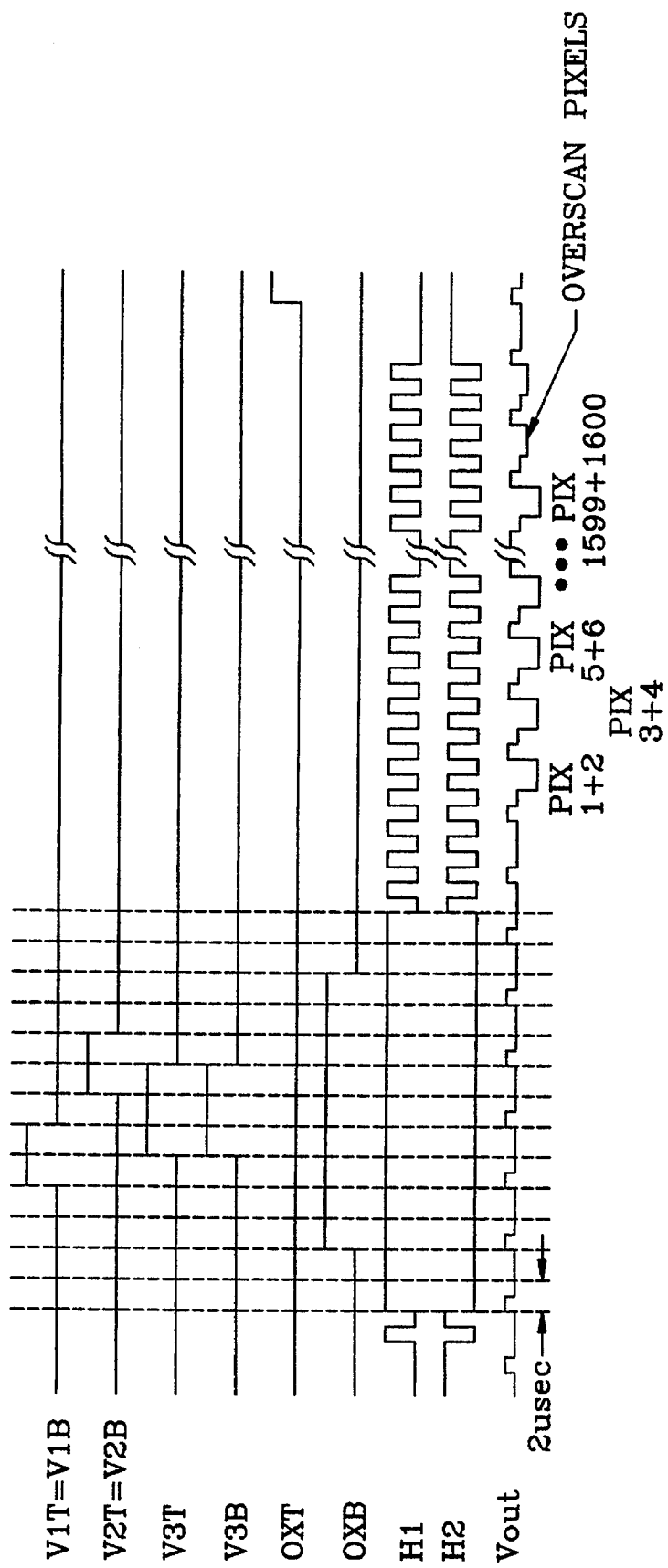
FIGS. 9A and 9B are timing diagrams that illustrate the vertical register timing for the bottom row readout and the top row readout, respectively.
Figure 9B:
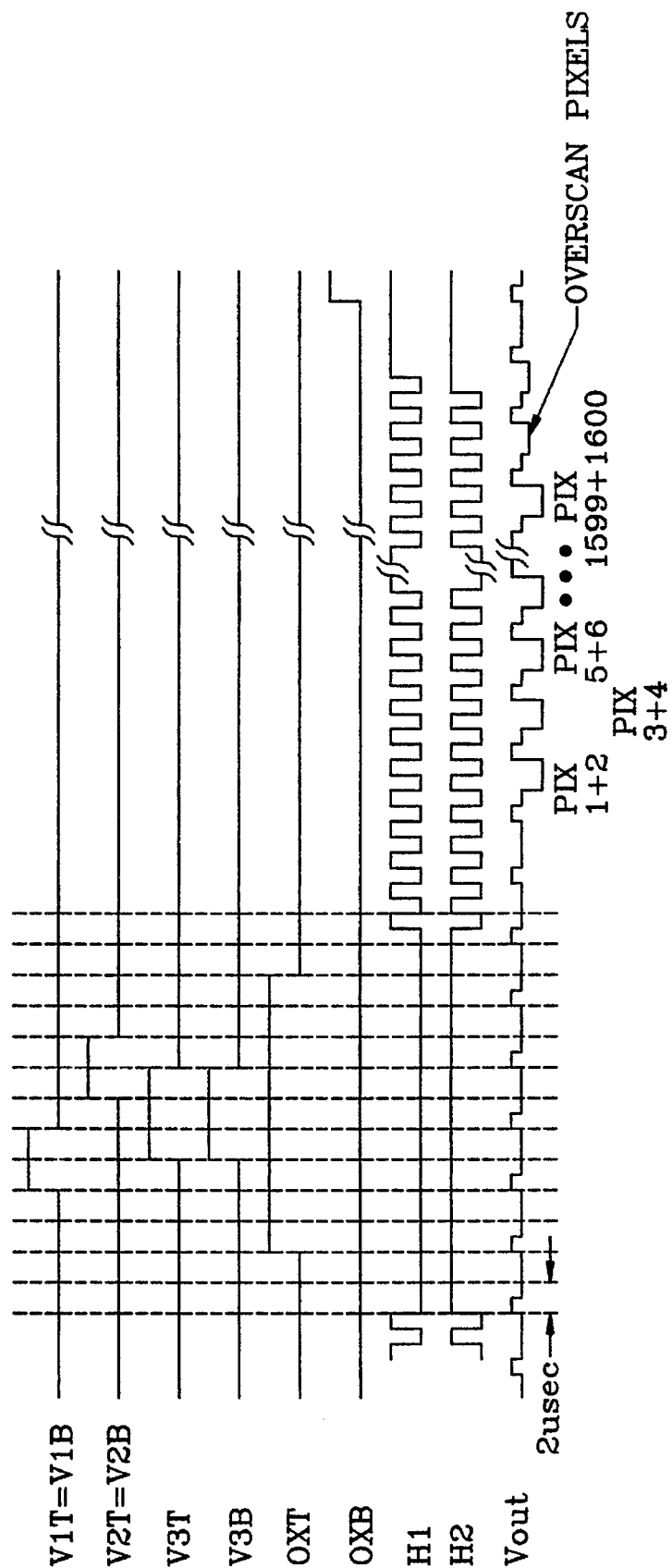
Figure 10A:
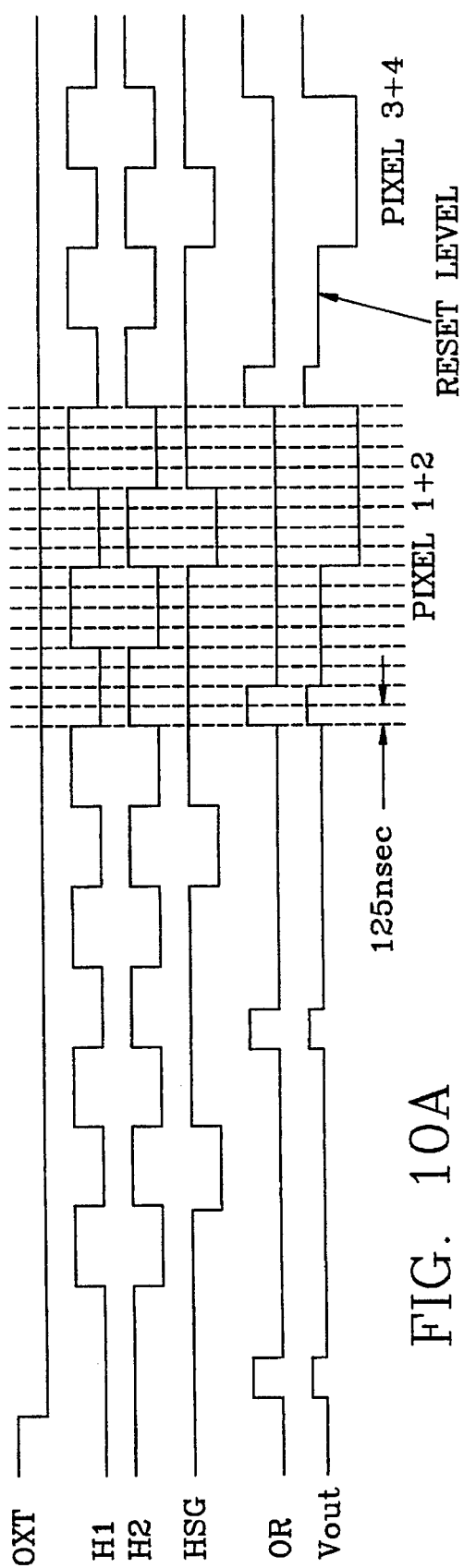
FIGS. 10A and 10B are timing diagrams that illustrate the horizontal register timing for the top row readout and the bottom row readout, respectively.
Figure 10B:
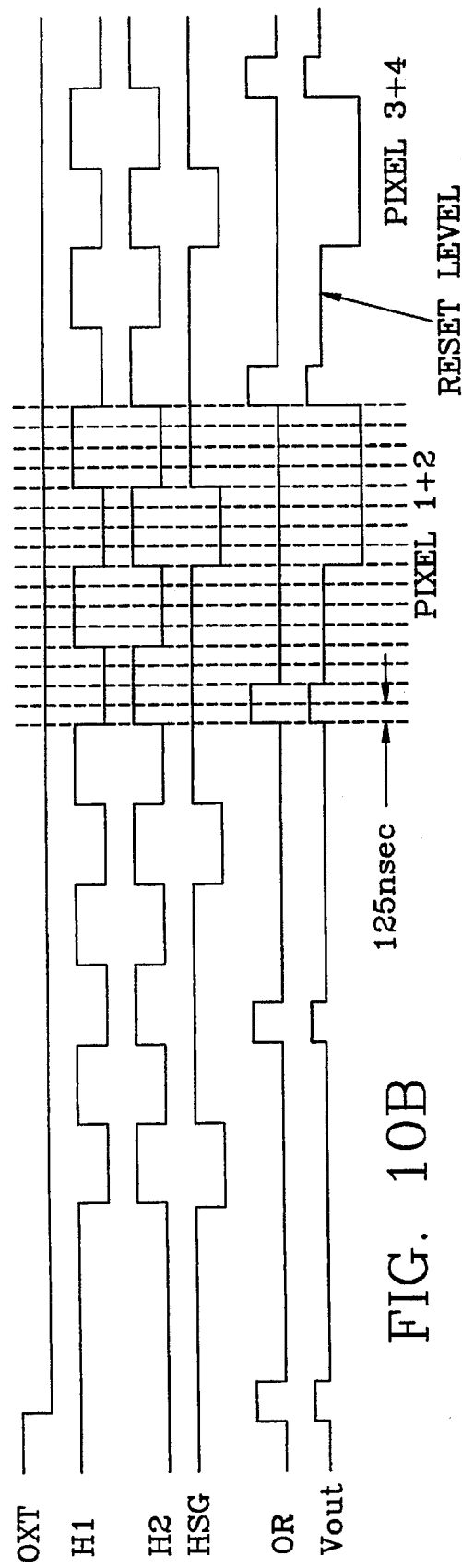

Reference is now made to FIG. 5 for showing a presently preferred full frame transfer CCD architecture in accordance with this invention. FIG. 5 depicts three-layer poly, three phase (V1, V2, V3B, V3T) vertical or parallel shift registers associated with pixels 20; a two-layer poly, two phase (H1, H2) serial (center read-out) horizontal shift register 10b associated with pixels 22; and two, two-layer poly (barrier/well) transfer gates 24 between the parallel and serial registers. The various dimensions shown in FIG. 5 are exemplary. FIG. 5 also illustrates a timed sequence (t1–t12) of charge packet movement towards the center read-out (horizontal) register 10b under control of the three phase clocks (V1, V2, V3B and V3T) that are coupled to associated gates.

In another embodiment, the parallel registers, i.e, those orthogonal to the center serial read-out register 10b, are comprised of smaller pixels which may or may not be summed (binned) in the read-out process. For example, the smaller pixels could be 20 microns square and each stage of the read-out register 10b could be exactly or approximately 20 microns×40 microns. This embodiment is desirable in that it provides multiple-use capability for the sensor. In the second use, there would be a small decrease in pixel density in the region of the center read-out register 10b.

In a variation of this last-mentioned embodiment, the holding stages of the parallel register are enlarged by a small amount so as to provide extra charge handling capability. These holding stages are shown in FIG. 5 as the 23 micron structures adjacent to the transfer gates.

FIGS. 4A–4C illustrate an intra-oral X-ray sensor package 30 and the associated cabling. More particularly, FIG. 4A is a front view, FIG. 4B is a side view, and FIG. 4C is a back view of the sensor package 30. The view of FIG. 4A shows the sensor array 10a and mounting substrate 12 as shown in FIG. 1. The center read-out register 10b is also illustrated in this view. The side and back views illustrate an inert dielectric outer package or casing or shell 32 that has a region 34 for containing interface electronics and to which an interface cable 36 is attached. The interface cable 36 conveys power, clocks and bias signals from an external device, and also conveys electrical signals representative of sensed charge packets to the external device. The interface electronics preferably includes a video cable driver for outputting the charge packets received from the preamplifier 10c of FIG. 1, and further includes pulse shaping circuits for sharpening the edges of the various clock signals that are received through the cable 36. The illustrated cabling arrangement for the compact oblong package allows ease of use in either a vertical or a horizontal orientation. A patient bite holder is not shown. The overall package has a size that can be incorporated within a patient's mouth. During use the CCD array 10a is not cooled, and is operated at ambient temperature.

Shown in FIG. 4B is a layer 38 of X-ray responsive material, such as MIN-R, and a fiber optic face plate 40 that is interposed between the film layer 38 and the radiation receiving surface of the array 10a. The fiber optic face plate 40 can be an unbiased plate (i.e., the fibers are oriented orthogonally to the surface of the array 10a), since an orthogonal alignment of the X-ray source to the CCD array is typically never achieved in a dental application. As such, direct illumination of the CCD array 10a with X-rays does not normally occur. A suitable thickness for the faceplate 40 is approximately one millimeter.

In accordance with an aspect of this invention the central read-out register 10b is used for exposure monitoring. A typical situation is that an estimated optimum exposure time is known to at least an accuracy of ±50%. In this case, the two phase clocks of the read-out register 10b are held stationary for, by example, 50% of the estimated optimum exposure time (e.g., 8 msec out of 16 msec), the photosensitive pixels of the center read-out register 10b are then read out, processed, and stored. As a part of the processing a new estimate is made of the optimum exposure time. If time permits, the center read-out register pixels can be read out and stored one or more additional times, and the optimum exposure time estimate updated. Eventually, the X-ray source is turned off, the three phase clocks are started, and the left and right halves of the array 10b are read out. Once the actual exposure time is known, or the actual number of X-ray source pulses is known, the stored signal amplitudes(s) from the central read-out register 10b are multiplied by a constant so as to match the other pixels.

For the above assumed conditions, the amplitudes of the signals read out from the pixels 22 of the center read-out register 10b are approximately doubled, and the noise content of the data is doubled also. In a typical exposure this noise will be dominated with shot noise from the photosignal and, as a result, the signal-to-noise ratio in the pixels 22 is degraded by only approximately 30%.

Referring now to the timing diagrams of FIGS. 7, 8, 9A, 9B 10A and 10B, a method for operating and reading out the array 10a is now described. In these Figures the term "overscan" refers to optionally providing additional clock pulses when clocking out a row (or half-row) of pixels. The additional clocks can be employed for reading-out diagnostic related information.

In a first method of this invention the three phase vertical register clocks and the two phase read-out (horizontal) register clocks are run so as to flush out dark current. When the exposure is initiated the vertical clocks and the horizontal register clocks are stopped and the array 10a is exposed to the X-ray radiation to register an image from the resulting light generated by the layer 38. During the exposure the center read-out register 10b can be periodically monitored as described above so as to determine the optimum exposure time. After the exposure the first line from the top half of the imaging area 10a is transferred into the read-out register 10b. This line is then clocked out to the output amplifier 10c. After the first line is completely read out, the first line from the bottom half of the imaging area 10a is transferred into the read-out register 10b and read out. This alternate read-out (top and bottom halves, or vice versa) is repeated until all the data is read-out from the entire array.

The presently preferred layout of the read-out register 10b requires the bus for the read-out register 10b to be located on top of itself. Therefore this register, although optically active, will have a reduced sensitivity. This forms a narrow "dead" line in the image which can be corrected for in the final image processing software, as described above.

A method to detect the beginning and end of the incoming illumination is now described in the context of the center read-out register embodiment of this invention, although it should be realized that the method is applicable to other full frame CCDs.

All parallel clocks are stopped during integration in the normal operation of a full frame transfer CCD. The read-out register clocks can either be stopped or continuously clocked during this integration period. If a conventional metal light shield is omitted from the design of the readout register, the read-out register can be used to either form a slice of the image, as in the case of the other rows of the imaging area (clocks stopped), or as a detector of the incoming illumination (clocks operating).

With the clocks operating and the light shield omitted, the output of the CCD can be monitored to detect both the beginning and end of illumination. An external threshold detection circuit (embodied with, by example, the image processor/controller 44 of FIG. 6) is used to determine these points. Prior to illumination the output is monitored and a background level is determined. This background level includes dark signal generation. When the illumination begins, and after some number of clock cycles, the threshold circuit detects an increase in signal and causes the clocking circuits for the parallel registers to cease clocking, thereby beginning an integration period. As the illumination ends, the same threshold detection methodology is used to detect the end of illumination (although there is no appreciable dark current signal from the parallel registers at this time). The clocking circuits are then triggered to generate clocks and a read-out sequence is initiated. The same or different threshold points can be used to detect the onset and termination of the exposure.

In the presently preferred embodiments of this invention the center read-out register 10b is not light shielded and, as a result, can function both to detect the onset and termination of an exposure, and also to monitor the exposure so as to optimize the exposure time. Furthermore, any accumulated charge read out of the center read-out register 10b during the exposure, either for exposure optimization and/or exposure termination detection, is preferably saved and subsequently used to complete the image within the central stripe occupied by the read-out register.

Furthermore, the serial read-out register 10b is positioned at an optimum location (i.e., at the center of the array) for monitoring the exposure, and also for detecting the onset and termination of the exposure.

FIG. 6 is a block diagram of a dental X-ray system 40 in accordance with this invention. The intra-oral sensor package 30 is connected through the cable 36 to a clock/bias generator 42. The clock/bias generator 42 outputs the necessary three phase parallel register clocks, the two phase central read-out register clocks, the transfer gate clock, and any other required clocks, biases, and operating power. The clock/bias generator 42 also outputs digitized image pixel data to the before-mentioned image processor/controller 44 wherein processing of the image is performed. An optional graphic display 46 is connected to an output of the image processor/controller 44 for viewing an image that results from an exposure. A memory device (not shown) may also be coupled to the image processor/controller 44 for storing digital data obtained from an exposure.

In accordance with an aspect of this invention an X-ray source 48 is connected to the image processor/controller 44 and at least an on/off state of the source 48 is controlled thereby. It is further within the scope of this invention to have the image processor/controller 44 modify an X-ray flux density of the X-ray source 48 in accordance with the accumulated charge that is read out of the photo-responsive pixels 22 of the centrally located read-out register 10b prior to the termination of the exposure. In this regard reference is made to the previous description of the center read-out register exposure monitoring method that enables an optimum exposure time to be established for each X-ray image.

The chamfered corners of the intra-oral sensor package 30 enable a reduction in the overall volume of the package and furthermore eliminates sharp corners. The end result is an increase in patient comfort during the exposure.

It should be realized that the teaching of this invention can also be applied to other applications wherein a small image sensor is desired, and wherein it is desirable to shape the sensor to conform to some non-square, non-rectangular configuration. One such application is an endoscope application wherein the chamfered corners enable the image sensor package to be better accommodated within a circular outline of the endoscope.

It should further be realized that the teaching of this invention is not limited to three phase CCD parallel registers, nor to two phase CCD serial registers.

Thus, while the invention has been particularly shown and described with respect to preferred embodiments thereof, it will be understood by those skilled in the art that changes in form and details may be made therein without departing from the scope and spirit of the invention.

What is claimed is:

1. A CCD image sensor, comprising:

an array of first photo-responsive elements comprising a plurality of rows, the first photo-responsive elements being responsive to first multi-phase clock signals for shifting photo-induced charge packets along said rows;

a centrally disposed read-out register comprised of second photo-responsive elements and disposed orthogonally to said rows for dividing said array into a first half and a second half each comprised of a plurality of half rows, said read-out register being coupled to individual ones of said half rows of said first and second halves of said array by first and second transfer gates, respectively, and responsive to at least one second clock for serially shifting, to an output port, charge packets received from said half rows through said first and second transfer gates; and a charge-sensing amplifier located at said output port for generating output voltages proportional in size to a magnitude of said charge packets, said charge-sensing amplifier being located adjacent to an edge of said array and away from a corner of said array.

2. An image sensor as set forth in claim 1 wherein at least one corner of said array is chamfered.

3. An array as set forth in claim 1 wherein corners of said array are chamfered such that said array has a generally octagonal shape.

4. An array as set forth in claim 1 wherein said rows operate with a three phase clock and wherein said read-out register operates with a two phase clock.

5. An array as set forth in claim 1 wherein said read-out register is capable of operating independently of said rows of first photo-responsive elements for serially outputting to said charge-sensing amplifier charge packets generated only by said second photo-responsive elements.

6. An array as set forth in claim 1 and further comprising:

a first read-out register clock signal path running parallel to said centrally disposed read-out register along a first side of said second photo-responsive elements; and a second read-out register clock signal path running parallel to said centrally disposed read-out register along a second side of said second photo-responsive elements.

7. A method for operating an image sensor to record illumination resulting from an X-ray exposure, comprising the steps of:

providing an array of radiation sensors comprising a plurality of parallel register rows of first photo-responsive pixels that are optically coupled to an X-ray responsive light source, the array further comprising a centrally disposed read-out register comprised of second photo-responsive pixels that are optically coupled to the X-ray responsive light source, the centrally disposed read-out register being orthogonally oriented to the parallel register rows for dividing said array into a first half and a second half, each comprised of a plurality of parallel register half rows, the read-out register being coupled to individual ones of the half rows for receiving photo-induced charge packets therefrom;

initiating an X-ray exposure having an initial estimated exposure time;

during the X-ray exposure, accumulating photo-induced charge within individual ones of the first and second photo-responsive pixels;

at a time prior to a termination of the predetermined exposure time, reading out first accumulated photo-induced charge from the second pixels of the centrally disposed read-out register; and modifying, if appropriate, the initial estimated exposure time in accordance with a magnitude of the first accumulated photo-induced charge that is read out from the second pixels.

8. A method as set forth in claim 7 wherein the step of reading out includes a step of storing digital data expressive of the magnitude of the first accumulated photo-induced charge that is read out from the second pixels, and further comprising the steps of:

at the end of the X-ray exposure, reading out second accumulated photo-induced charge from individual ones of the second pixels and reading out accumulated photo-induced charge from individual ones of the first pixels;

deriving an image from the accumulated photo-induced charge that is read out from the first pixels, and from the stored first accumulated photo-induced charge and the second accumulated photo-induced charge that is read out of the second pixels.

9. A method as set forth in claim 7 and further including a step of, at the end of the X-ray exposure, reading out accumulated photo-induced charge from individual ones of the first pixels by reading out the first half row and then the second half row of each of the parallel register rows.

10. A method for operating an image sensor to record illumination resulting from an X-ray exposure, comprising the steps of:

providing an array of radiation sensors comprising a plurality of parallel register rows of first photo-responsive pixels that are optically coupled to an X-ray responsive light source, the array further comprising a centrally disposed read-out register comprised of second photo-responsive pixels that are optically coupled to the X-ray responsive light source, the centrally disposed read-out register being orthogonally oriented to the parallel register rows for dividing said array into a first half and a second half, each comprised of a plurality of parallel register half rows, the read-out register being coupled to individual ones of the half rows for receiving photo-induced charge packets therefrom;

initiating an X-ray exposure having an initial X-ray flux density;

during the X-ray exposure, accumulating photo-induced charge within individual ones of the first and second photo-responsive pixels;

at a time prior to a termination of the X-ray exposure, reading out first accumulated photo-induced charge from the second pixels of the centrally disposed read-out register; and modifying, if appropriate, the initial X-ray flux density in accordance with a magnitude of the first accumulated photo-induced charge that is read out from the second pixels.

11. A method as set forth in claim 10 wherein the step of reading out includes a step of storing digital data expressive of the magnitude of the first accumulated photo-induced charge that is read out from the second pixels, and further comprising the steps of:

at the end of the X-ray exposure, reading out second accumulated photo-induced charge from individual ones of the second pixels and reading out accumulated photo-induced charge from individual ones of the first pixels;

deriving an image from the accumulated photo-induced charge that is read out from the first pixels, and from the stored first accumulated photo-induced charge and the second accumulated photo-induced charge that is read out of the second pixels.

12. A method as set forth in claim 10 and further including a step of, at the end of the X-ray exposure, reading out accumulated photo-induced charge from individual ones of the first pixels by reading out the first half row and then the second half row of each of the parallel register rows.

13. A method for operating an image sensor to record illumination resulting from an X-ray exposure, comprising the steps of:

providing an array of radiation sensors comprising a plurality of parallel register rows of first photo-responsive pixels that are optically coupled to an X-ray responsive light source, the array further comprising a centrally disposed read-out register comprised of second photo-responsive pixels that are optically coupled to the X-ray responsive light source, the centrally disposed read-out register being orthogonally oriented to the parallel register rows for dividing said array into a first half and a second half, each comprised of a plurality of parallel register half rows, the read-out register being coupled to individual ones of the half rows for receiving photo-induced charge packets therefrom;

prior to initiating an X-ray exposure, operating array clocking signals to read out charge packets at least from the second pixels of the centrally disposed read-out register;

comparing a magnitude of the charge packets to a first threshold magnitude;

when the first threshold magnitude is exceeded, determining that an X-ray exposure has been initiated;

terminating the operation of the array clocking signals; and during the X-ray exposure accumulating photo-induced charge within individual ones of the first and second photo-responsive pixels.

14. A method as set forth in claim 13 and further comprising the steps of:

operating the array clocking signals to read out photo-induced charge from the second pixels of the centrally disposed read-out register;

storing digital data expressive of the magnitude of photo-induced charge that is read out from the second pixels of the centrally disposed read-out register;

comparing a magnitude of the read out charge to a second threshold magnitude;

when the magnitude of the read out charge is less than the second threshold magnitude, determining that the X-ray exposure has been terminated;

operating the array clocking signals to read out any further accumulated photo-induced charge from individual ones of the second pixels and reading out accumulated photo-induced charge from individual ones of the first pixels; and deriving an image from the accumulated photo-induced charge that is read out from the first pixels, and from the stored photo-induced charge and the further accumulated photo-induced charge that is read out of the second pixels.

15. An intra-oral CCD X-ray image sensor, comprising:

an enclosure having a size that fits within a patient's mouth during an X-ray exposure, said enclosure having a plurality of chamfered corners;

a region of X-ray responsive light emitting material contained within said enclosure;

an uncooled CCD array that is optically coupled to said region of X-ray responsive light emitting material and that is contained within said enclosure, said array comprising first photo-responsive elements comprising a plurality of rows, the first photo-responsive elements being responsive to first multi-phase clock signals for shifting photo-induced charge packets along said rows;

said array further comprising a centrally disposed read-out register comprised of second photo-responsive elements and disposed orthogonally to said rows for dividing said array into a first half and a second half each comprised of a plurality of half rows, said read-out register being coupled to individual ones of said half rows of said first and second halves of said array by first and second transfer gates, respectively, and responsive to at least one second clock for serially shifting, to an output port, charge packets received from said half rows through said first and second transfer gates;

a charge-sensing amplifier located at said output port for generating output voltages proportional in size to a magnitude of said charge packets, said charge-sensing amplifier being located adjacent to an edge of said array and away from a corner of said array; and means for coupling clock signals to said array from an external clock signal source and for coupling the output voltages to an external image processing means.

16. An intra-oral CCD X-ray image sensor as set forth in claim 15 wherein a plurality of corners of said array are chamfered and are accommodated within said chamfered corners of said enclosure.

17. An intra-oral CCD X-ray image sensor as set forth in claim 15 wherein said rows operate with a three phase clock and wherein said read-out register operates with a two phase clock.

18. An intra-oral CCD X-ray image sensor as set forth in claim 15 wherein said read-out register is capable of operating independently of said rows of first photo-responsive elements for serially outputting to said charge-sensing amplifier charge packets generated only by said second photo-responsive elements, and wherein said charge packets are indicative of at least an initiation and a termination of an X-ray exposure.

19. An intra-oral CCD X-ray image sensor as set forth in claim 15 wherein said read-out register is capable of operating independently of said rows of first photo-responsive elements for serially outputting to said charge-sensing amplifier charge packets generated only by said second photo-responsive elements, and wherein said charge packets are indicative of at least a cumulative X-ray exposure dosage prior to a termination of an X-ray exposure.

20. An intra-oral CCD X-ray image sensor as set forth in claim 15, and further comprising a fiber optic assembly for optically coupling said uncooled CCD array to said region of X-ray responsive light emitting material.

\* \* \* \* \*